(12) United States Patent
Li

(10) Patent No.: US 10,932,494 B2
(45) Date of Patent: Mar. 2, 2021

(54) UPPER-ASSEMBLY ELECTRONIC CIGARETTE ATOMIZER, ELECTRONIC CIGARETTE CONTAINING THE SAME, AND METHODS OF ASSEMBLY THEREOF

(71) Applicant: SHENZHEN INNOKIN TECHNOLOGY CO., LTD, Shenzhen (CN)

(72) Inventor: Jian Wei Li, Shenzhen (CN)

(73) Assignee: SHENZHEN INNOKIN TECHNOLOGY CO., LTD, Shenzen (CN)

( * ) Notice: Subject to any disclaimer, the term of this patent is extended or adjusted under 35 U.S.C. 154(b) by 239 days.

(21) Appl. No.: 15/345,630

(22) Filed: Nov. 8, 2016

(65) Prior Publication Data
US 2017/0347705 A1    Dec. 7, 2017

(30) Foreign Application Priority Data

Jun. 7, 2016    (CN) ............................ 20162054025.4
Aug. 8, 2016    (EP) .................................... 16183160

(51) Int. Cl.
*A24F 47/00*    (2020.01)
*A61M 15/00*    (2006.01)
*A61M 15/06*    (2006.01)
*A61M 11/04*    (2006.01)

(52) U.S. Cl.
CPC ......... *A24F 47/008* (2013.01); *A61M 11/042* (2014.02); *A61M 15/0023* (2014.02); *A61M 15/0025* (2014.02); *A61M 15/06* (2013.01)

(58) Field of Classification Search
CPC ...... A23F 47/00; A23F 47/002; A23F 47/008; A23F 47/004; A23F 1/28; A23F 7/02; A23F 13/02
See application file for complete search history.

(56) References Cited

U.S. PATENT DOCUMENTS

2016/0100633 A1*    4/2016    Gao ..................... A24F 47/008
131/329

FOREIGN PATENT DOCUMENTS

KR    20110056905 A    *    5/2011
WO    WO-2015149311 A1    *    10/2015    ............ A61M 11/08

OTHER PUBLICATIONS

Kim "KR 20110056905, machine translation", published Nov. 8, 2011.*
Liu, "WO 2015/149311, machine translation", published Oct. 8, 2015.*
Oct. 13, 2017 Extended European Search Report for corresponding French App. No. EP 16 18 3160.

* cited by examiner

*Primary Examiner* — Alex B Efta
(74) *Attorney, Agent, or Firm* — Mei & Mark LLP

(57) ABSTRACT

An upper-assembly electronic cigarette atomizer is provided. The atomizer may include a liquid storage cup having an upper opening, and a head cover component connected with the upper opening in a threaded manner. The liquid storage cup and the head cover component may form a closed space for containing an e-liquid. The head cover component may be configured to be detached from the liquid storage cup as an integral unit. An electronic cigarette containing an upper-assembly electronic cigarette atomizer and a method of assembly are also provided.

8 Claims, 5 Drawing Sheets

UPPER-ASSEMBLY ELECTRONIC CIGARETTE ATOMIZER, ELECTRONIC CIGARETTE CONTAINING THE SAME, AND METHODS OF ASSEMBLY THEREOF

CROSS-REFERENCE TO RELATED APPLICATION

This application claims priority to, and incorporates herein in their entireties, Chinese Application No. 201620545025.4, filed on Jun. 7, 2016 and European Application No. 16183160.7, filed on Aug. 8, 2016.

TECHNICAL FIELD

The present invention relates to electronic cigarette devices, in particular to an upper-assembly, open-injection, and fully enclosed electronic cigarette atomizer; to a fully enclosed electronic cigarette including the upper-assembly atomizer; and to assembly methods of the same.

BACKGROUND

Existing electronic cigarettes generally include a battery box formed by a battery and a control circuit board, which is then connected to other electronic cigarette components, such as an atomizer and a cigarette holder (aka drip-tip or mouthpiece). The structure of a conventional electronic cigarette atomizer is generally as follows: A circular atomizing core and a connecting pipe are arranged in the central position in a circular enclosed space, and the remaining annular space is used to hold an e-liquid (a liquid to be atomized within an atomizer device). The atomization core and the connecting pipe are also closed; two symmetrical liquid inlet holes are arranged on the outer wall of the atomizing core to supply the e-liquid to the atomizing core. Through its connection to the battery box, an electric heating device in the atomizing core heats so that the e-liquid that enters the atomization core is atomized and may be aspirated through the connecting pipe.

In order to electrically connect the atomization core and the battery box, the atomizer and the battery box are provided with a special connection mechanism. For example, an externally threaded conductive column may be arranged at the lower portion of the atomizer, and an internally threaded conductive opening may be provided at the top of the battery box. The function of the electronic cigarette can be realized only if the conductive column and the battery box are electrically connected through a threaded connection. Therefore, an atomizer is generally powered from its lower portion. To provide power to the lower portion, atomization and heating components—including the atomization core of the atomizer—are typically located at the at the lower portion of the atomizer. With the atomization core arranged at the lower portion, an air inlet, which communicates with the atmosphere and is used for introducing fresh air, is also arranged at the lower portion.

Due to this configuration, e-liquid in the atomizer is prone to leak through the air inlet, leading to pollution and waste. Thus. during e-liquid injection, particular attention must be paid to the problem of liquid leakage through the lower air inlet hole. In addition, due to this configuration, with air intake and power supply located in the lower portion, it is difficult to replace the atomization core.

However, as long as the atomizer is powered from its lower portion, the atomization core has to be assembled in the lower part. And, as long as air intake is provided through the lower portion of the atomizer, liquid leakage through the air inlet remains a major risk. In addition, such a structure with air intake and power supply from the lower portion is complicated. This makes conventional electronic cigarette assembly and disassembly difficult.

SUMMARY

The present disclosure provides an upper-assembly electronic cigarette atomizer, which improves over conventional electronic cigarette atomizers by overcoming one or more problems of the prior art, as described above. Embodiments of the disclosed upper-assembly electronic cigarette atomizer and electronic cigarette containing the same improve over the prior art by, for example, providing a fully closed cartridge that prevents e-liquid leakage. The upper-assembly electronic cigarette atomizer provides an upper-assembly structure that may permit the supply of electrical power and air intake from its upper portions, making assembly and disassembly easier. In addition, such an upper-assembly structure may make e-liquid injection more convenient and safer.

In one embodiment, an upper-assembly electronic cigarette atomizer is provided. The atomizer may include a liquid storage cup having an upper opening, and a head cover component connected with the upper opening in a threaded manner. The liquid storage cup and the head cover component may form a closed space for containing an e-liquid. The head cover component may be configured to be detached from the liquid storage cup as an integral unit.

In another embodiment, the head cover component may include a cigarette holder, a liquid storage cup cover, connecting electrodes, an aspiration pipe, an air intake pipe, and an atomization device. The aspiration pipe, the air intake pipe, and the atomization device may extend into the liquid storage cup.

In one embodiment, an upper-assembly electronic cigarette atomizer is provided. The atomizer may include a liquid storage cup having an upper opening and a head cover component connected with the upper opening. The head cover component may include a cigarette holder, a liquid storage cup cover, connecting electrodes, an aspiration pipe, an air intake pipe, and an atomization device. The aspiration pipe, the air intake pipe, and the atomization device extended into the liquid storage cup.

In another embodiment, the liquid storage cup cover may have a multilayer structure, including a liquid storage cup cover body, an insulating ring disposed upon the liquid storage cup cover body, an air intake annular chamber having an upper cover and disposed upon the insulating ring, and an air intake regulating ring disposed upon the air intake annular chamber. The liquid storage cup cover body may be annularly and electrically connected with the air intake pipe. The air intake annular chamber cover and the aspiration pipe may be annularly and electrically connected. The air intake regulating ring may be configured to rotate with respect to the air intake annular chamber.

In yet another embodiment, the atomization device may include an atomizing core body and an outer shell.

In yet another embodiment, the atomizing core body may be secured within the outer shell. An upper end of the atomizing core body may be annularly connected with a lower end of the aspiration pipe in an electrically insulated manner that does not block the lower end of the aspiration pipe. An upper end of the outer shell may be annularly and electrically connected with a lower end of the air intake pipe. An atomizing core body may further include a radial liquid inlet and an outer wall with a ventilation notch. An electric heating device may be disposed within the atomizing core body. The outer shell may further include a radial inlet hole positioned to align with of the liquid inlet of the atomizing core body and an inner wall. The outer wall of the atomizing core body may contact and electrically connect to the inner wall of the outer shell. The ventilation notch may be disposed within the inner wall of the outer shell. The electric heating device may be electrically connected with the atomizing core body and the aspiration pipe, respectively.

In yet another embodiment, the atomizing core body may include an outer wall with a ventilation notch. The ventilation notch may be disposed axially and may be depressed towards an axis of the atomizing core body. The sides of the ventilation notch may be in contact with an inner wall of the outer shell.

In yet another embodiment, the outer shell may include a cylindrical portion and a cup-shaped portion. The cylindrical portion and the cup-shaped portion may be interconnected. The atomizing core body may be fixedly disposed within the outer shell. The cylindrical upper end of the outer shell may be annularly connected to the air intake pipe.

In yet another embodiment, the cylindrical portion of the outer shell may be sheathed upon an outer wall of the atomizing core body. The cup-shaped portion and a lower end of atomizing core body may be interconnected in a threaded manner. The cylindrical portion of said outer shell and the air intake pipe may be interconnected in a threaded manner.

In yet another embodiment, the upper-assembly electronic cigarette atomizer may further include a buffer insulating ring group and a buffer ventilating ring group. The buffer insulating ring group may be disposed between the atomizing core body and the aspiration pipe. The buffer ventilating ring group may be disposed between the atomizing core body and a cup-shaped portion bottom of the outer shell. An upper portion of the buffer ventilating ring group may be provided with an axial hole. A lower portion of the buffer ventilating ring may be provided with a radial hole. The axial hole may communicate with the radial hole. A bottom of the buffer ventilating ring group may be pressed tightly against a bottom of the cup-shaped portion of the outer shell.

In yet another embodiment, an electronic cigarette is provided. The electronic cigarette may include the upper-assembly electronic cigarette atomizer and a battery box.

In one embodiment, a method of assembling of an atomizer is provided. The atomizer includes a liquid storage cup with an upper opening and a head cover component connected to the upper opening of the liquid storage cup to form a closed space. The head cover component includes a liquid storage cup cover body, connecting electrodes, an aspiration pipe, and an air intake pipe in an upper portion. The head cover component also includes an atomization device. The method includes separately assembling the atomization device and the upper part of the head cover component, and connecting the assembled atomization device to a lower end of the air intake pipe.

In another embodiment, a method of assembling of an atomizer further includes installing a buffer ventilating ring group in a lower part of an atomizing core body, installing a cup-shaped portion of an outer shell on the lower part of the atomizing core body, installing a sealing ring around the atomizing core body, installing a cylindrical portion of the outer core, and installing a buffer insulating ring group onto the atomizing core body.

In yet another embodiment, assembly of the upper part of the head cover component may be accomplished by providing an air intake regulating ring, providing an air intake annular chamber, disposing the air intake annular chamber upon the insulating ring, disposing the insulating ring upon a liquid storage cup cover body, and connecting the liquid storage cup cover body with the air intake pipe.

In one embodiment a method of assembling of an electronic cigarette is provided. The electronic cigarette includes an upper-assembly electronic cigarette atomizer, which has a liquid storage cup with an upper opening. The method includes providing e-liquid and placing the e-liquid into the liquid storage cup through the upper opening, connecting the head cover component to the liquid storage cup to form the upper-assembly electronic cigarette atomizer, and connecting the upper-assembly electronic cigarette atomizer to a battery box.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and aspects of the apparatuses and methods described herein and, together with the description, serve to explain the principles of the invention.

DETAILED DESCRIPTION

Reference will now be made in detail to the present exemplary embodiments, examples of which are illustrated in the accompanying drawings. Wherever possible, the same reference numbers will be used throughout the drawings to refer to the same or like parts. While the description includes exemplary embodiments, other embodiments are possible, and changes may be made to the embodiments described without departing from the spirit and scope of the invention. The following detailed description does not limit the invention. Instead, the scope of the invention is defined by the appended claims and their equivalents.

Throughout this disclosure, relative positional language, such as "upper", "lower", "above", "below", and the like, shall be understood to refer to the relative positions of structural elements as depicted in FIGS. 1-5.

Figure 6:
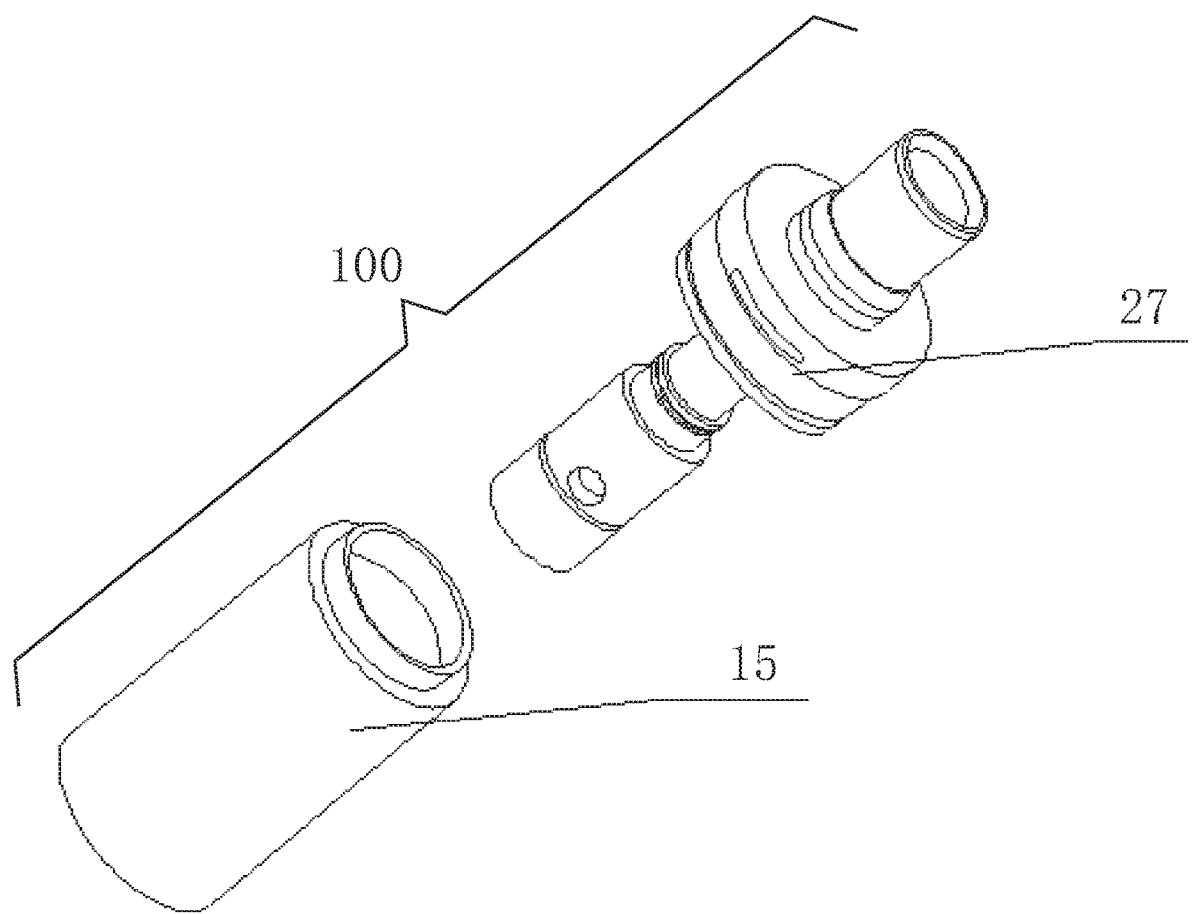
FIG. 6 shows a perspective view of an exploded upper-assembly electronic cigarette atomizer according to an exemplary embodiment.

As shown in FIG. 6, upper-assembly electronic cigarette atomizer 100 may include a head cover component 27 and a liquid storage cup 15 having an upper opening. Head cover component 27 and the upper opening of liquid storage cup 15 may be connected, for example in a threaded manner, to form an enclosed space. The enclosed space may be provided with an e-liquid to form a cartridge. As this cartridge is completely closed, e-liquid leakage may be prevented.

Figure 1:
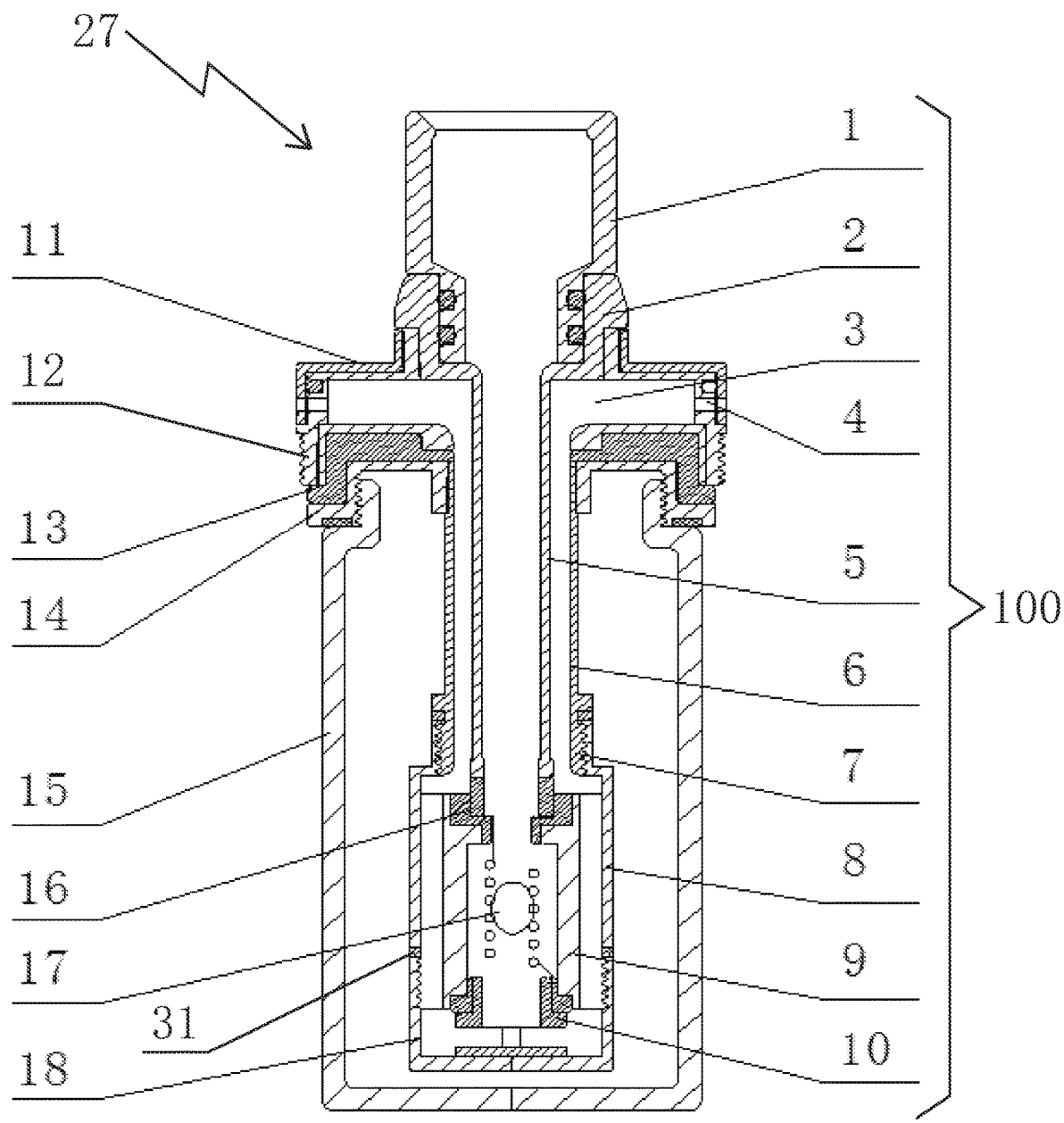
FIG. 1 shows a cross-sectional view of an upper-assembly electronic cigarette atomizer according to an exemplary embodiment.

FIG. 1 provides a cross-sectional view of upper-assembly electronic cigarette atomizer 100, including head cover component 27 and liquid storage cup 15. Head cover component 27 comprises a cigarette holder 1, a liquid storage cup cover, connecting electrodes, an aspiration pipe 5, an air intake pipe 6, and an atomization device. The atomization device, the aspiration pipe 5, and the air intake pipe 6 extend into the liquid storage cup 15 and remain surrounded by e-liquid during use. When the head cover component 27 is disconnected from the liquid storage cup 15, for example, by unscrewing the components from one another, the entire head cover component 27 is advantageously removed as single assembled device. The cartridge can thereby easily be refilled with an e-liquid.

Figure 2:
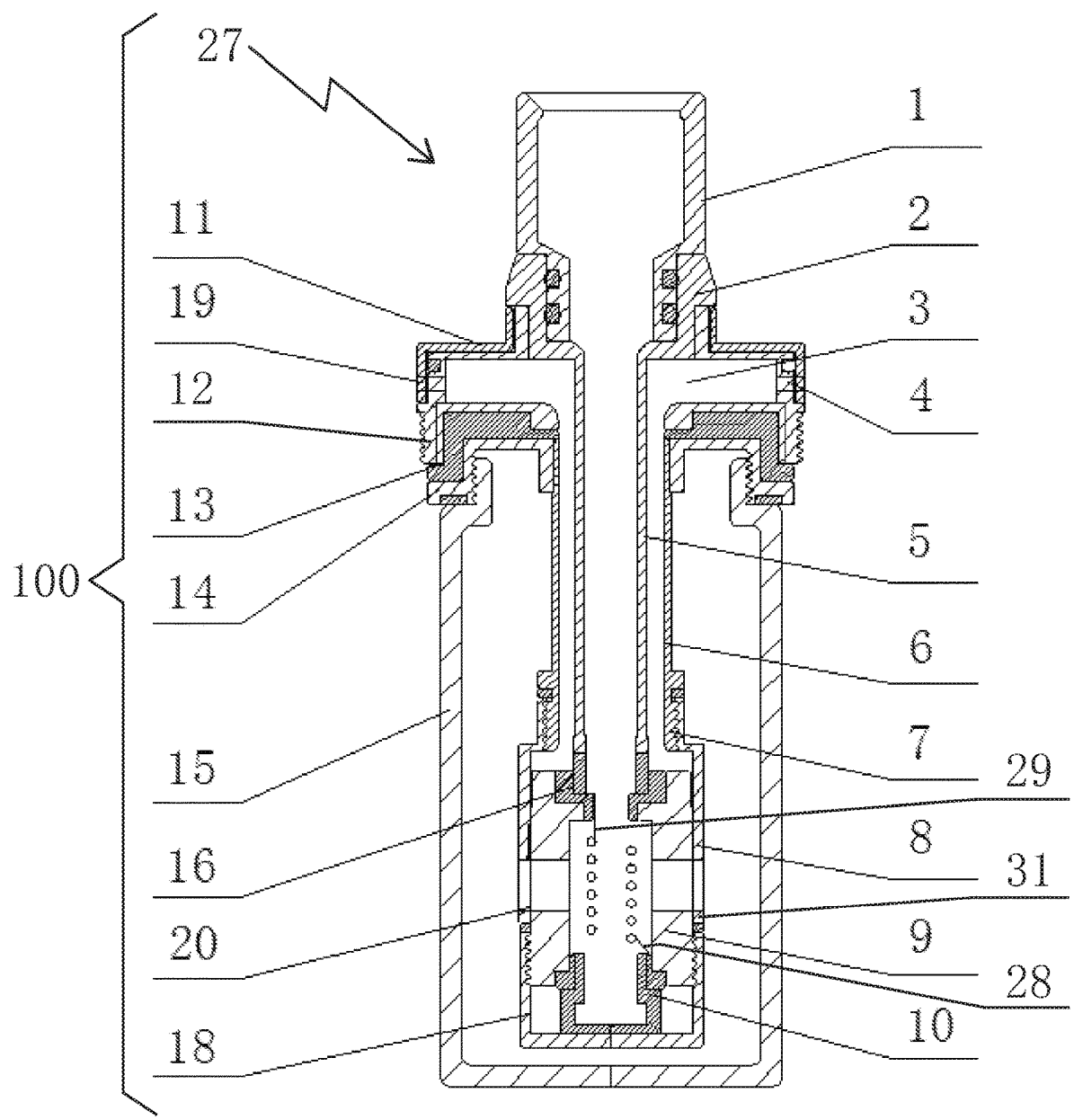
FIG. 2 shows another cross-sectional view of the upper-assembly electronic cigarette atomizer of FIG. 1, wherein the upper-assembly electronic cigarette atomizer is axially rotated by an angle of 90 degrees.

As shown in FIGS. 1 and 2, an atomization device may comprise an atomizing core body 9 and an outer shell, which further comprises a cylindrical portion 8 and a cup-shaped portion 18. The cup-shaped portion 18 may be tightly connected with the cylindrical portion 8 to form an outer shell with a closed bottom. Sealing ring 31 may be disposed between cup-shaped portion 18 and cylindrical portion 8 as part of this tight connection. The upper end of the cylindrical portion 8 of the outer shell may be connected with an air intake pipe 6 by an internal screw thread 7. Thus, the outer shell 8, 18 of the atomization device may be connected with the air intake pipe on a threaded and sealed manner. The atomizing core body 9 of the atomization device may be disposed within the outer shell.

Figure 3:
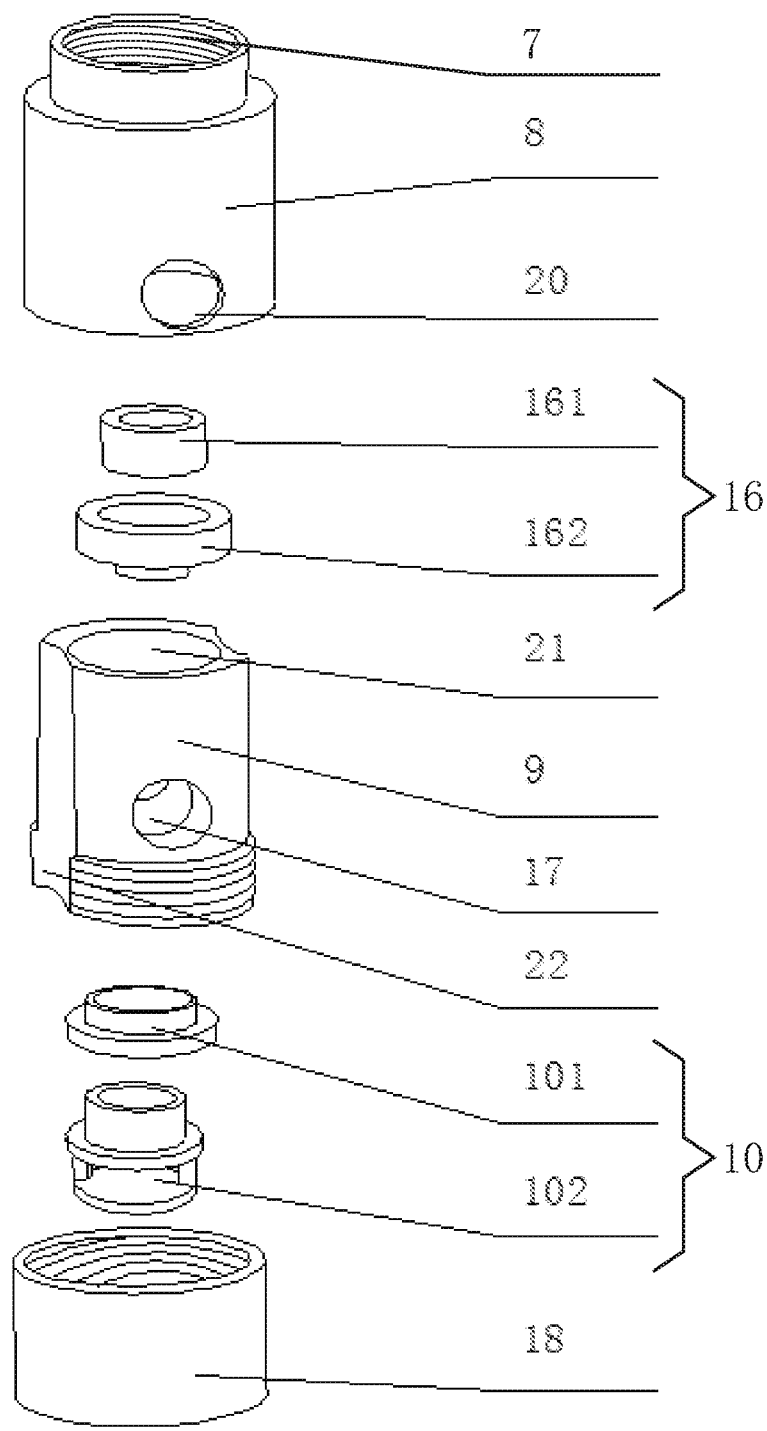
FIG. 3 shows an exploded view of portions of an atomization device according to an exemplary embodiment.
Figure 4:
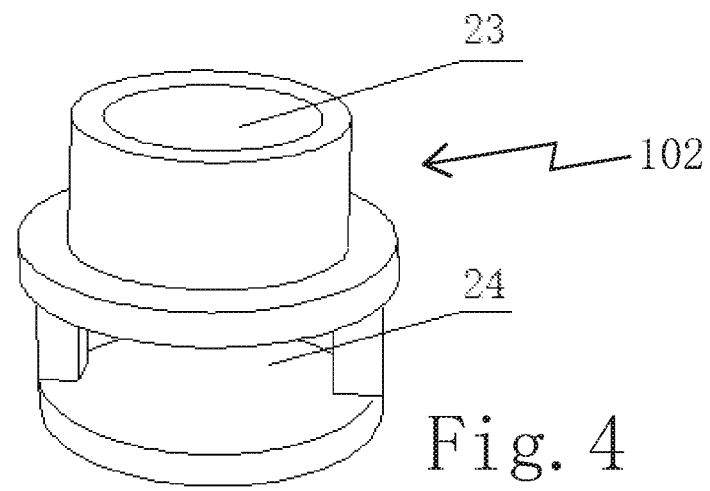
FIG. 4 shows a perspective view of a ventilating ring according to an exemplary embodiment.

As shown in FIG. 3, the atomizing core body 9 may be a cylindrical element with its body having a circular cross-section. Atomizing core body 9 may be provided with an axial atomization airway 21. In the axial atomization airway 21, an electric heating device may be arranged—for example, comprising a resistance wire heater (depicted in FIGS. 1, 2, and 5) and a liquid-guiding wick (not shown)—as would be understood by a person of skill in the art. In addition, at least one radial liquid inlet 17 may be provided on a wall of the atomizing core body 9. The liquid inlet 17 may be used for guiding an e-liquid with or without a liquid-guiding wick.

Further, as shown in FIGS. 1 and 2, the atomizing core body 9 may be assembled such that it is tightly pressed against the interior of the outer shell. Specifically, the outer wall of the atomizing core body 9 may be tightly pressed against the inner wall of the outer shell. Consequently, e-liquid leakage into air intake pipe 6 may be substantially prevented.

With reference to FIG. 3, the outer wall of the atomizing core body 9 may include axial ventilation notch 22 depressed towards the central axis of body 9. The axial ventilation notch 22 may be used to draw air from above atomizing core body 9, where it may be provided by into air intake pipe 6, to below atomizing core body 9, where it may be received within cup-shaped portion 18. Cylindrical portion 8 of the outer shell may include an outer shell liquid inlet 20 positioned corresponding to the liquid inlet 17 of atomizing core body 9 to lead an e-liquid into the atomizing core body 9.

With further reference to FIG. 3, a closed connection between the cylindrical portion 8 of the outer shell and the cup-shaped portion 18 may be implemented as follows: In the outer portion of the lower section of the atomizing core body 9, an external thread maybe provided. A corresponding internal thread may be provided on the internal upper portion of cup-shaped portion 18. Through such threading, atomizing core body 9 may be connected to the cup-shaped portion 18. In order to achieve a stronger liquid sealing effect, sealing ring 31 may be arranged at the joint (shown in FIGS. 1, 2 and 5, but not shown FIG. 3).

As shown in FIGS. 1 and 2, atomization device may include buffer insulating ring group 16 in order to ensure that the installation position of the atomizing core body 9 in the outer shell is fixed and stable. Buffer insulating ring group 16 may be disposed upon the upper side of the atomizing core body 9 and may be pressed tightly against the bottom of the aspiration pipe 5. Buffer insulating ring group 16 may include a buffer pressure ring 161 and an insulating ring 162, as depicted in FIG. 3, but alternatively may comprise a single integral element in other embodiments. Buffer insulating ring group 16 may be made of insulating materials with certain compression capabilities, such as silica gel. The purpose of buffer insulating ring group 16 is to ensure that the connection between atomizing core body 9 and aspiration pipe 5 is mechanically secure with appropriate buffering of mechanical pressure and that those components are electrically insulated from one another.

As shown in FIGS. 1, 2, and 3, the lower part of atomizing core body 9 may be disposed upon a buffer ventilating ring group 10. Buffer ventilating ring group 10 may be disposed within cup-shaped portion 18 of the outer shell of the atomizer. As shown in FIG. 3, the buffer ventilating ring group 10 may comprise buffer ring 101 and ventilating ring 102, but alternatively may comprise a single integral element in other embodiments. Both rings may be made of insulating materials with a certain compression capability, such as silica gel. As shown in further detail FIG. 4, the top of the ventilating ring 102 may be provided with an axial ventilating hole 23 that communicates with the atomization airway 21 of atomizing core main body 9. Additionally, the lower end of the ventilating ring 102 may be provided with a radial ventilating hole 24. Axial ventilating hole 23 and the radial ventilating hole 24 may communicate with each other through an internal cavity of ventilating ring 102. The threaded, secure engagement between cup-shaped portion 18 and atomizing core body 9 may be mechanically buffered by those components' mutual engagement with buffer ventilating ring group 10. Buffer ventilating ring group 10 permits the flow of air from the bottom portion of ventilation notch 22 of atomizing core body 9 to atomization airway 21 of atomizing core body 9.

As shown in FIGS. 1 and 2, the atomization device is a combination of elements arranged at the lowermost end of the head cover component 27. The atomization device is connected to other elements of head cover component 27 through aspiration pipe 5 and air intake pipe 6. The connection may be implemented by connecting outer shell cylindrical portion 8 to the lower end of air intake pipe 6 through screw thread 7. In addition, buffer insulating ring group 16 at the upper part of atomizing core body 9 may be tightly pressed against the lower end of aspiration pipe 5.

The liquid storage cup cover of the head cover component 27 may have a multilayer structure, including liquid storage cup cover body 14 and insulating ring 13. The bottom layer of the liquid storage cup cover may be liquid storage cup cover body 14. Liquid storage cup cover body 14 may be an annular structure that may be annularly and electrically connected with the upper end of the air intake pipe 6. The upper layer of liquid storage cup cover may be insulating ring 13.

Air intake annular chamber 3 may be disposed above insulating ring 13. Annular chamber 3 may include an upper layer with a side wall and a lower layer. The upper layer may be annularly and electrically connected to the aspiration pipe 5. The side wall of air intake annular chamber 3 may be provided with an air inlet 4. Air intake regulating ring 11 may be arranged externally to the sidewall. Air intake regulating ring 11 may rotate relative to the annular chamber 3 and its sidewall. Air intake regulating ring 11 may be provided with air intake regulating hole 19, which may fully or partially align with air inlet 4 depending on the rotation of air intake regulating ring 11 with respect to air inlet 4. In this manner, the passage of air through air inlet 4 and air intake regulating hole 19 may be adjusted to regulate the air flow rate.

Figure 5:
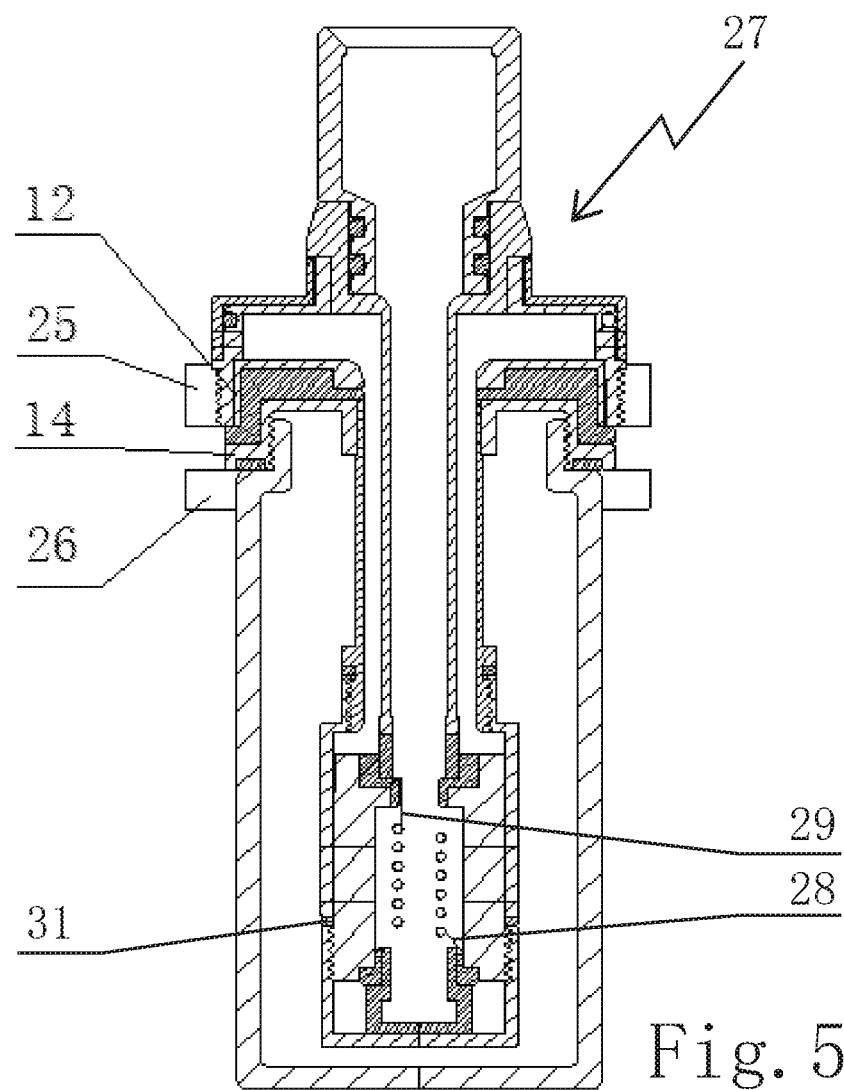
FIG. 5 shows a partial cross-sectional view of an electronic cigarette that includes the upper-assembly electronic cigarette atomizer of FIG. 1.

With reference to FIG. 5, exemplary electrical connections between upper-assembly electronic cigarette atomizer and a battery box are discussed. Liquid storage cup cover body 14 may be a conductor with an annular structure. The lower side of the annular outer edge of liquid storage cup cover body 14 may be provided with a connection contact shoulder. Ventilating annular chamber 3 may be comprised of conductive material, with an external portion of its side wall including connection thread 12. With such an arrangement, head cover component 27 may be connected to a battery box through the screw thread 12 in a threaded manner. Thus, a battery box or similar device may connect to upper-assembly electronic cigarette atomizer 100 through (1) a lower electrode 26 that may be pressed tightly against, and electrically connect with, the connection contact shoulder of the liquid storage cup 14; and (2) an upper electrode 25, which may be securely and electrically connected to the screw thread 12.

Liquid storage cup cover body 14, which, as noted above, may be connected to lower electrode 26, is electrically connected to air intake pipe 6, which in turn is electrically connected to the outer shell 8, 18 of the atomization device. Ultimately, atomizing core body 9 conductively contacts the outer shell 8, 18 to electrically connect lower electrode 26 with the electric heating device of the atomizer via lower lead 28. Upper electrode 25 conducts to the outer wall of ventilating annular chamber 3 through screw thread 12, which conducts through the upper cover of annular chamber 3, and on to aspiration pipe 5. Ultimately, upper lead 29 at the lower end of the aspiration pipe 5 is electrically connected to the electric heating device in the atomizing core body 9.

An electronic cigarette atomizer in accordance with embodiments of the present disclosure may be assembled as follow: The atomization device arranged at the lowermost end of the head cover component 27 and the upper part of the head cover component 27 may be assembled separately and then joined. One purpose of dividing the outer shell of the atomization device into two parts 8, 18 is to facilitate assembly.

The atomization device may be assembled as follows: Buffer ventilating ring group 10 may be disposed onto the lower part of the atomizing core body 9. Then, outer shell cup-shaped portion 18 may be attached to the lower part of atomizing core body 9 via threading. Subsequently, a sealing ring 31 may be optionally installed around the atomizing core body 9, upon outer shell cup-shaped portion 18. Then, cylindrical portion 8 of the outer shell may be disposed upon sealing ring 31, or directly upon outer shell cup-shaped portion 18. Then, buffer insulating ring group 16 may be disposed upon atomizing core body 9 within cylindrical portion 8 of the outer shell to complete assembly of the atomization device.

The upper part of the head cover component 27 may be assembled as follows: The upper end of the aspiration pipe 5 may be provided with connecting tube 2 used for mounting cigarette holder 1. Cigarette holder 1 may optionally be installed within aspiration pipe 2. The annular platform of connecting pipe 2 (e.g., a lower surface perpendicular to and surrounding the vertical internal passageway of aspiration pipe 5) may be used as an installation platform. Air intake regulating ring 11 may be mounted upon (e.g., below) annular platform of the connecting pipe 2. Then, air intake annular chamber 3 may be disposed upon (e.g., underneath) air intake regulating ring 11. Insulating ring 13 may be disposed upon (e.g., underneath) the lower layer of the air intake annular chamber 3. Then, liquid storage cup cover body 14 may be arranged upon (e.g., underneath and within) insulating ring 13. Subsequently, air intake pipe 6 may be tightly fitted within the innermost annular wall of liquid storage cup cover body 14, thereby creating a fixed connection.

The atomization device arranged at the lowermost end of the head cover component 27 and the upper part of the head cover component 27 may be securely joined. For example, the external connection threads 7 at the base of air intake pipe 6 may be engaged with the internal threads at the upper part of outer shell cylindrical portion 8.

Once head cover component 37 is assembled as described above, a functioning electronic cigarette with upper-assembly electronic cigarette atomizer 100 may be assembled. First, an e-liquid may be injected or otherwise provided into liquid storage cup 15. Then, liquid storage cup 15 may be attached to head cover component 27 to complete assembly of an upper-assembly electronic cigarette atomizer 100, for example, via engagement of internal threading of liquid storage cup cover body 14 and external threading in an upper portion of liquid storage cup 15. Then, an electronic cigarette battery box may be installed on the upper-assembly electronic cigarette atomizer 100 to complete assembly of an electronic cigarette. The electrodes of the battery box may electrically connect with connection thread 12 and the connection contact shoulder at the lower side of the annular outer edge of liquid storage cup cover body 14, respectively.

An electronic cigarette with upper-assembly electronic cigarette atomizer 100 may operate as follows. First, the power supply function of the battery may be switched on via an electronic cigarette battery box. Then, a portion of e-liquid in the liquid storage cup 15 may enter atomization airway 21 of the atomizing core via outer shell liquid inlet 20 and liquid inlet 17 of the atomizing core body 9. This e-liquid may be atomized by the electric heating device and aspirated by the user. Fresh air may enter through air inlet 4 of the side wall of the air intake annular chamber 3 and air intake regulating hole 19 of air intake regulating ring 11, and may flow toward the atomization device through the annular space between air intake pipe 6 and aspiration pipe 5. In the atomization device, the fresh air may reach bottom of atomization airway 21, where it may be facilitate continued atomization and aspiration of e-liquid, via flow through ventilating notch 22 of the atomizing core body 9 and buffer ventilating ring group 10. The flow rate of fresh air may be adjusted by a user rotating air intake regulating ring 11 rotate relative to the other components of head cover component 27, which alters the respective alignment between with air inlet 4 of the sidewall of air intake annular chamber 3 and air intake regulating hole 19 of air intake regulating ring 11 to increase or decrease the size of the collective fresh air passageway.

The above-disclosed upper-assembly electronic cigarette atomizer 100 and an electronic cigarette containing the same improve over the prior art by, for example, providing a fully closed cartridge that prevents e-liquid leak. The above-disclosed upper-assembly electronic cigarette atomizer 100 provides an upper-assembly structure that may permit the supply of electrical power and air intake from its upper portions, making assembly and disassembly easier. In addition, such an upper-assembly structure may make e-liquid injection more convenient and safer.

Although the foregoing embodiments have been described in detail by way of illustration and example for purposes of clarity of understanding, it will be readily apparent to those of ordinary skill in the art in light of the description herein that certain changes and modifications may be made thereto without departing from the spirit or scope of the appended claims. It is also to be understood that the terminology used herein is for the purpose of describing particular aspects only, and is not intended to be limiting, since the scope of the present invention will be limited only by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of ordinary skill in the art upon reading this disclosure, each of the individual aspects described and illustrated herein has discrete components and features which may be readily separated from or combined with the features of any of the other several aspects without departing from the scope or spirit of the disclosure. Any recited method can be carried out in the order of events recited or in any other order that is logically possible. Accordingly, the preceding merely provides illustrative examples. It will be appreciated that those of ordinary skill in the art will be able to devise various arrangements which, although not explicitly described or shown herein, embody the principles of the disclosure and are included within its spirit and scope.

Furthermore, all examples and conditional language recited herein are principally intended to aid the reader in understanding the principles of the invention and the concepts contributed by the inventors to furthering the art, and are to be construed without limitation to such specifically recited examples and conditions. Moreover, all statements herein reciting principles and aspects of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary configurations shown and described herein.

In this specification, various preferred embodiments have been described with reference to the accompanying drawings. It will be apparent, however, that various other modifications and changes may be made thereto and additional embodiments may be implemented without departing from the broader scope of the claims that follow. The specification and drawings are accordingly to be regarded in an illustrative rather than restrictive sense.

I claim:

1. An upper-assembly electronic cigarette atomizer, comprising:
   a liquid storage cup having an upper opening; and
   a head cover component connected with the upper opening in a threaded manner,
   wherein:
   the liquid storage cup and the head cover component form a closed space for containing an e-liquid;
   the head cover component is configured to be detached from the liquid storage cup as an integral unit;
   the head cover component comprises a mouthpiece, a liquid storage cup cover, connecting electrodes, an aspiration pipe, an air intake pipe, and an atomization device;
   the aspiration pipe, the air intake pipe, and the atomization device extended into the liquid storage cup;
   the liquid storage cup cover comprises a multilayer structure including a liquid storage cup cover body, an insulating ring disposed upon the liquid storage cup cover body, an air intake annular chamber having an upper cover and disposed upon the insulating ring, and an air intake regulating ring disposed upon the air intake annular chamber;
   the liquid storage cup cover body is annularly and electrically connected with the air intake pipe;
   the air intake annular chamber cover and the aspiration pipe are annularly and electrically connected; and
   the air intake regulating ring is configured to rotate with respect to the air intake annular chamber.

2. The upper-assembly electronic cigarette atomizer of claim 1, wherein the atomization device comprises an atomizing core body and an outer shell.

3. The upper-assembly electronic cigarette atomizer of claim 2, wherein:
   the atomizing core body is secured within the outer shell;
   an upper end of the atomizing core body is annularly connected with a lower end of the aspiration pipe in an electrically insulated manner that does not block the lower end of the aspiration pipe;
   an upper end of the outer shell is annularly and electrically connected with a lower end of the air intake pipe;
   the atomizing core body further comprises a radial liquid inlet and an outer wall with a ventilation notch;
   an electric heating device is disposed within the atomizing core body;
   the outer shell further comprises a radial inlet hole positioned to align with the liquid inlet of the atomizing core body and an inner wall;
   the outer wall of the atomizing core body contacts and electrically connects to the inner wall of the outer shell;
   the ventilation notch is disposed within the inner wall of the outer shell; and
   the electric heating device is electrically connected with the atomizing core body and the aspiration pipe, respectively.

4. The upper-assembly electronic cigarette atomizer of claim 2, wherein:
   the atomizing core body comprises an outer wall with a ventilation notch;
   the ventilation notch is disposed axially and is depressed towards an axis of the atomizing core body; and
   sides of the ventilation notch are in contact with an inner wall of the outer shell.

5. The upper-assembly electronic cigarette atomizer of claim 2, wherein:

the outer shell comprises a cylindrical portion and a cup-shaped portion, the cylindrical portion and the cup-shaped portion being interconnected;

the atomizing core body is fixedly disposed within the outer shell; and a cylindrical upper end of the outer shell is annularly connected to the air intake pipe.

6. The upper-assembly electronic cigarette atomizer of claim 5, wherein:

the cylindrical portion of the outer shell is sheathed upon an outer wall of the atomizing core body;

the cup-shaped portion and a lower end of atomizing core body are interconnected in a threaded manner;

the cylindrical portion of said outer shell and the air intake pipe are interconnected in a threaded manner.

7. The upper-assembly electronic cigarette atomizer of claim 2, further comprising a buffer insulating ring group and a buffer ventilating ring group, wherein:

the buffer insulating ring group is disposed between the atomizing core body and the aspiration pipe;

the buffer ventilating ring group is disposed between the atomizing core body and a cup-shaped portion bottom of the outer shell;

an upper portion of the buffer ventilating ring group is provided with an axial hole, a lower portion of the buffer ventilating ring group is provided with a radial hole;

the axial hole communicates with the radial hole;

a bottom of the buffer ventilating ring group is pressed against a bottom of the cup-shaped portion of the outer shell.

8. An electronic cigarette, comprising:

the upper-assembly electronic cigarette atomizer of claim 1; and a battery box.

* * * * *